United States Patent [19]

Margolis

[11] Patent Number: 4,707,233
[45] Date of Patent: Nov. 17, 1987

[54] DEVICE FOR EXTRACTION OF ELECTROPHORETIC FRACTIONS
[75] Inventor: Joel Margolis, Greenwich, Australia
[73] Assignee: Gradiant Pty Limited, Greenwich, Australia
[21] Appl. No.: 856,786
[22] Filed: Apr. 28, 1986
[30] Foreign Application Priority Data
Apr. 29, 1985 [AU] Australia ............... PH0347
[51] Int. Cl.⁴ ............................................. G01N 27/28
[52] U.S. Cl. ............................ 204/182.3; 204/182.8; 204/299 R; 204/301
[58] Field of Search ............ 204/182.3, 182.8, 299 R, 204/301

[56] References Cited
U.S. PATENT DOCUMENTS
3,751,356 8/1973 Takeya et al. ............... 204/182.3
4,243,507 1/1981 Martin et al. ............... 204/299 R
4,401,538 8/1983 Hausfeld ..................... 204/299 R FOREIGN PATENT DOCUMENTS
2148325 5/1985 United Kingdom ........... 204/182.3

Primary Examiner—John F. Niebling
Assistant Examiner—Terryence Chapman
Attorney, Agent, or Firm—Michael J. Striker

[57] ABSTRACT

A method and device for the preparative scale recovery of a protein or other charged macromolecule by electrophoretic separation of a mixture of such macromolecules. The device is adapted to be installed between the electrodes of an electrophoretic cell and includes a gel receiving receptacle adapted to hold the end of a gel slab or gel fragments containing an electrophoretically separated macromolecule. An aperture in the base of the receptacle is covered by a first membrane which is substantially permeable to the macromolecules desired to be recovered and a second membrane substantially impermeable to the macromolecules to be recovered but permeable to electrolyte molecules in a buffer solution used in electrophoresis. The two membranes lie in spaced apart array with one another to define therebetween a recovery space. Means are provided to allow the periodic or continuous withdrawal of buffer solution and macromolecules from the recovery space.

10 Claims, 3 Drawing Figures

DEVICE FOR EXTRACTION OF ELECTROPHORETIC FRACTIONS

BACKGROUND OF THE INVENTION

The present invention relates to a device and a method for the recovery of proteins and other macromolecules separated by electrophoresis through a suitable gel.

Electrophoresis involves the separation of charged molecular species in an electric field. Gel electrophoresis involves the migration of those charged molecular species through a porous gel under the applied electric field. The most widely used gel is polyacrylamide however other gels may also be used.

Although gel electrophoresis has been widely used for analysing mixtures of macromolecules, such as proteins, its use has not been matched by adoption of the method to preparative scale recovery of the macromolecules i.e. recovery in amounts typically of 1 to 50 mg.

SUMMARY OF THE INVENTION

The present invention relates to a device and method for preparative gel electrophoresis which avoids many of the problems encountered with known preparative gel electrophoresis techniques such as a requirement for extended incubation with solvents; low efficiency; contamination with gel polymers; denaturation of the recovered macromolecule; expense; and problems of heat build up within the gel.

The present invention consists in an electroelution device for use in the preparative scale recovery of macromolecules from a electrophoretic gel and adapted to be installed between the electrodes of an electrophoretic cell, comprising a gel receiving receptacle, an aperture in the base of the receptacle, a first membrane substantially permeable to the macromolecules desired to be recovered covering the aperture, a second membrane, substantially impermeable to the macromolecules to be recovered but permeable to electrolyte molecules in a buffer solution used in electrophoresis, lying in spaced apart array with the first membrane to define therebetween a recovery space, and means to allow the periodic or continuous withdrawal of buffer solution and macromolecules from the recovery space.

The present invention further consists in a method for the preparative scale recovery of macromolecules from an electrophoretic gel comprising placing an electrophoretic gel containing macromolecules to be recovered into the gel receiving receptacle of an electroelution device according to this invention, applying an electric potential across the device to cause the macromolecules to migrate through the first membrane into the recovery space and recovering the macromolecules from the recovery space of the said device.

As used herein the term electrophoresis means any non-denaturing cathodic or anodic electrophoresis including sodium dodecyl sulfate electrophoresis. Similarly references to electrophoretic gels include any type of such gel including gradient gels.

The device and method of the present invention may be used in two quite distinct ways. In a first method a zone of a conventional electrophoretic gel which is known to contain a macromolecular species is excised from the gel, fragmented, as by extrusion through a grid or the nozzle of a syringe, and the fragments placed in the gel receiving receptacle. The device is then placed in an electrophoretic cell and the macromolecules caused to migrate through the first membrane and into the recovery space from which a concentrated solution of the macromolecules may be withdrawn. A second, and much preferred, method involves inserting one end of a plate-like electrophoresis gel slab into the gel receiving receptacle of the device, applying a mixture of the macromolecules to be separated to the gel slab distal to the device and electrophoretically driving the macromolecules, or some of them, in sequence along the slab, through the first membrane and into the recovery space where each species of macromolecule may be separately recovered. The second method is particularly preferred as only a single electrophoretic step is required to prepare milligram quantities of purified macromolecules in high concentrations.

In a particularly preferred embodiment of the present invention the first and second membranes are formed of paper impregnated with a polyacrylamide gel. The gel in each case is so selected as to give the desired pore size to each of the membranes. The first membrane preferably has a pore size such that macromolecules of molecular weights of from 10,000 to 1,000,000 may pass through the membrane into the recovery space. The second membrane, by contrast, has very much smaller pores which prevent such macromolecules from passing out of the recovery space while still allowing the small ions carrying the electrophoretic electric current to pass through. The first and second membranes may be formed of other suitable materials known in the art. The first membrane could be formed of paper impregnated with agarose while the second may be conveniently formed of cellulose.

The recovery space is preferably very thin in order to obtain the highest possible concentration of the macromolecules within the space. The device must be provided with means to allow for the continuous or periodic recovery of buffer solution and macromolecules from the recovery space. In the simplest form of the invention an aperture is provided through which the needle of a syringe may be inserted into the recovery space to allow for the periodic recovery of material within the recovery space. In more sophisticated embodiments of the invention a fine tube is provided to extend into each end of the recovery space so that buffer solutions may be drawn through the recovery space continuously or discontinuously. As the buffer solution is drawn through the space it picks up and carries with it any macromolecules which have migrated into the space. In a particularly preferred operating procedure, after the device has been operational for a period the contents of the recovery space are pumped out and recovered, the recovery space is then flushed clean with buffer solutions and the pump then stopped until a further molecular species has collected in the recovery space. The process is then repeated. This process has the advantage that after each collection stage the recovery space is flushed clear of the previously collected macromolecular species thus ensuring that remnants of that species will not contaminate the next species of macromolecules collected.

The gel receiving receptacle and thus the membranes and the recovery space are preferably rectangular in a cross section transverse to the electrophoretic current, one dimension of the rectangle preferably being very substantially larger than the other such that this rectangular configuration facilitates heat dissipation from the electrophoretic gel if the electrophoresis is carried out simultaneously with collections of the macromolecules. Ideally in such processes electrophoretic gels of only 3 mm thickness are used, these gels are similar to those used for analytical purposes. This minimises heat build up while having the additional advantage that the electrophoretic mobility of the macromolecules in the preparative recovery device is identical with this mobility in purely analytical situations.

The present device and process is particularly suitable for the separation and recovery of proteins however it will be appreciated that other charged macromolecules can also be similarly separated and recovered.

Hereinafter given by way of example are preferred embodiments of the present invention described with reference to the accompanying drawings in which:

DETAILED DESCRIPTION OF THE PREFERRED EMBODIMENT

Figure 1:
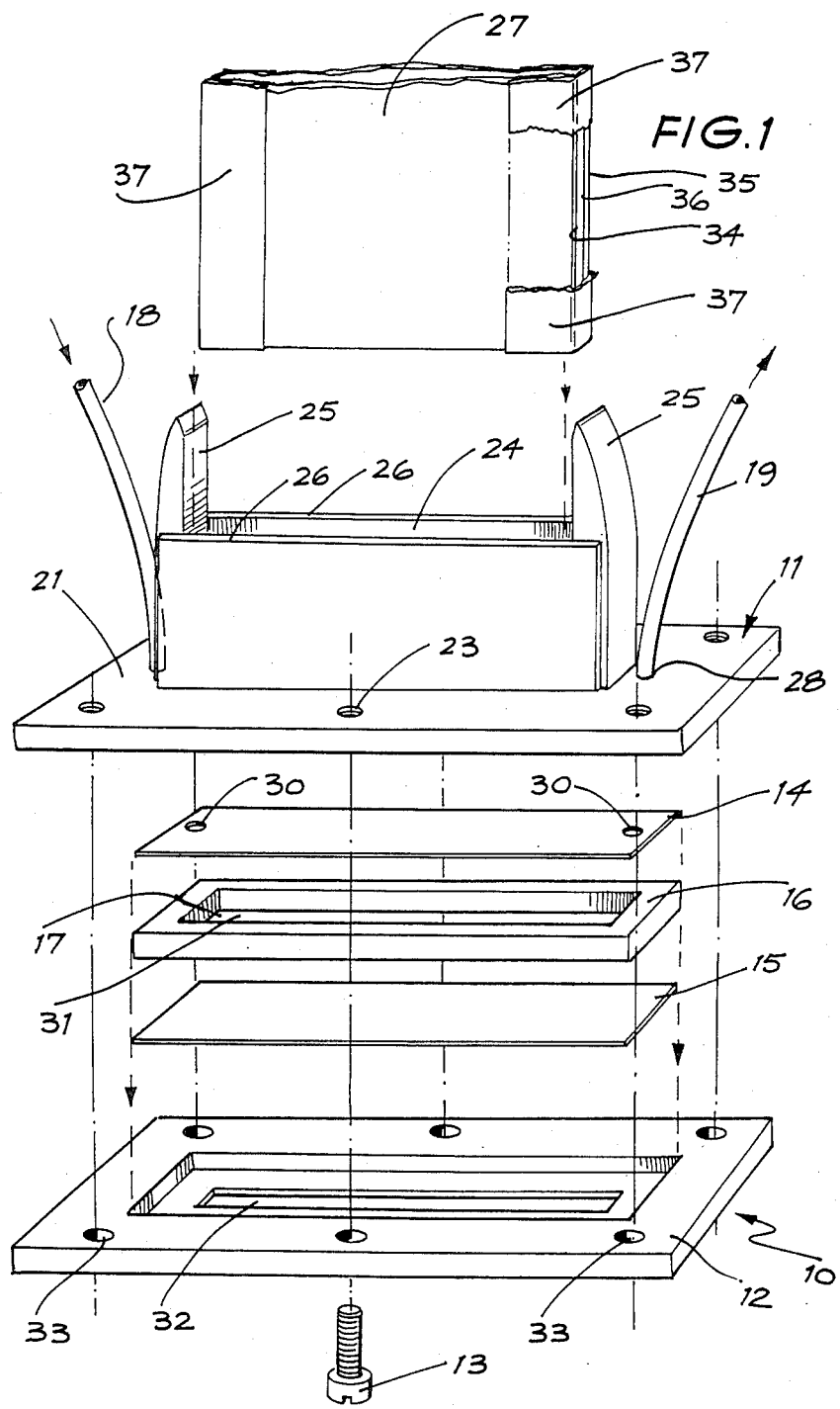
FIG. 1 is an exploded perspective view of a device according to the present invention.
Figure 2:
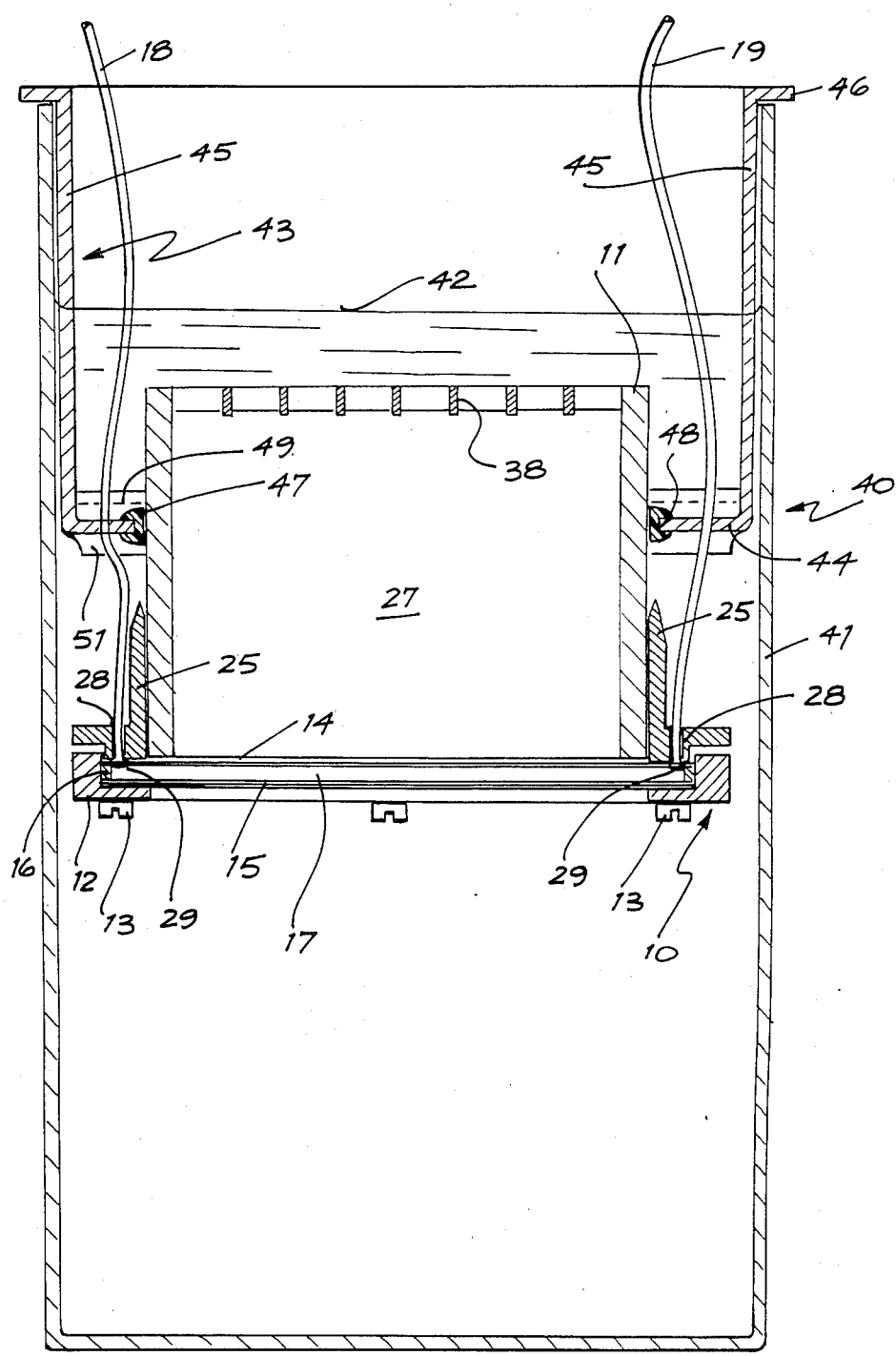
FIG. 2 is a vertical sectional view through the device of FIG. 1 when installed in an electrophoretic cell.

The device 10, as shown in FIGS. 1 and 2, comprises a housing 11 and a base plate 12 adapted to be clamped together by a plurality of screws 13. Two membranes 14 and 15, separated by a spacer 16, are adapted to be clamped between the housing 11 and the base plate 12 and to define a recovery space 17 between the membranes 14 and 15. Tubes 18 and 19 respectively serve to convey a buffer liquid into and out of the recovery space 17.

The housing 11 comprises a plate 21 having a rectangular hole 22 formed therein as well as a plurality of threaded holes 23 to receive the screws 13. The hole 22 is surrounded by four walls to define a gel receiving receptacle 24. The end walls 25 extend upwardly above the side walls 26 and are biassed inwardly to grip the side edges of an electrophoretic gel slab 27 (described hereinafter) inserted into the gel receiving receptacle 24.

As is best seen in FIG. 2 each of the tubes 18 and 19 extends through a hole 28 in the plate 21 adjacent a respectively one of the end walls 25 and terminates in an enlargement 29 (see FIG. 2) preventing the tubes 18 or 19 from being withdrawn from holes 28.

The membranes 14 and 15 are each formed of paper impregnated with cross-linked polyacrylamide. The amount of polyacrylamide and the amount of cross-linking agent is so selected that the desired macromolecules will be able to pass through the membrane 15. Both membranes, obviously, must be permeable to the electrolyte molecules in the buffer solution used in the electrophoretic cell in which the present device is to be used. The membrane 14 includes at either end a hole 30 through which one of the tubes 18 and 19 may project into the recovery space 17.

The membranes 14 and 15 are separated by the spacer 16 which has a rectangular aperture 31. The recovery space 17 is defined by the side edges of the aperture 31 in spacer 16 and the two membranes 14 and 15.

The base plate 12 includes a rectangular aperture 32 and a plurality of apertures 33 through which screws 13 may project. A recessed area of base plate 12 surrounds the aperture 32 and is adapted to locate the membranes 14 and 15 and the spacer 16.

The gel slab 27 comprises two planar sheets of glass 34 and 35 between which is a layer (typically 3 mm in thickness) of polyacrylamide gel 36. The slab 27 is held together along each side edge by a strip of adhesive tape 37 (which has been removed in part on the right hand side of slab 27 in FIG. 1 to show the construction of that slab). As is seen in FIG. 2 a sample holder 38 may be positioned in the upper end of gel slab 27.

The device 10 is used in an electrophoretic cell 40 such as that shown in FIG. 2. The cell 40 comprises a container 41 for a suitable buffer solution 42. Suspended in the container 41 is an electrode and gel slab holder 43 having a base 44 and four side walls 45. An outwardly projecting lip 46 at the upper end of the side walls 45 supports the holder 43 in container 41. The base 44 of the holder 43 is formed with a rectangular aperture 47 surrounded by a silicone rubber sealing strip 48 adapted to sealingly engage with a gel slab 27 pushed through aperture 47. The base 44 supports on its upper surface a first electrode wire 49 and on its underside a second electrode wire 51. The construction is such that any electric current must flow through the gel slab 27 and device 10 in transversing from one electrode to the other In use the slab 27 and device 10 are positioned within the cell 40 and the electrodes connected to a source of electric potential such that a current flows between the first and second electrodes 49 and 51. Upon the correct polarity being selected for the electrodes any charged molecules placed in the sample holder 38 will be drawn through the gel slab 27 into the receiving space 17. Due to the differential mobility of different species an electrophoretic separation of a mixture of molecular species may be achieved in the gel and the individual molecular species recovered separately and sequentially from the recovery space 17.

Figure 3:
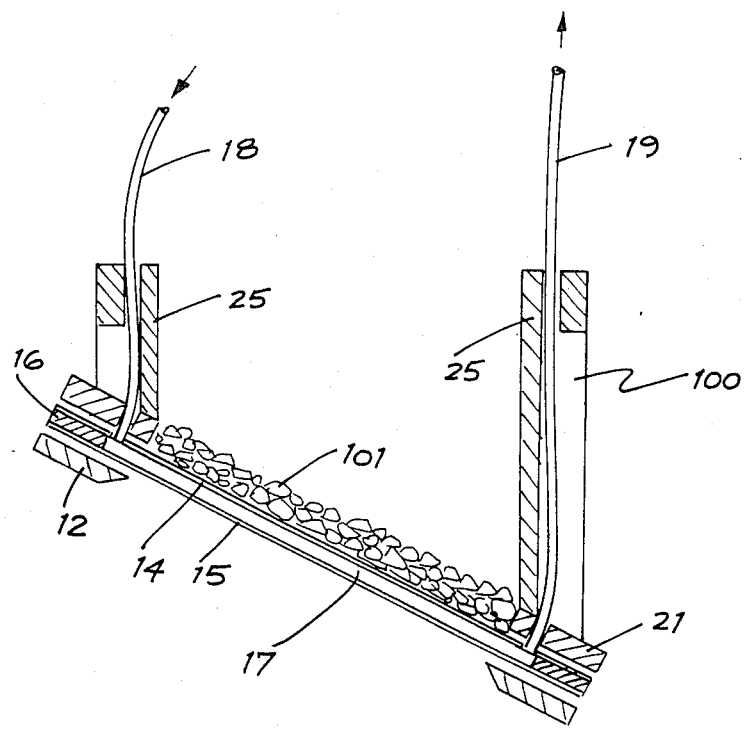
FIG. 3 is a vertical sectional view through a further embodiment of a device according to this invention.

The device 100 shown in FIG. 3 is essentially the same as device 10 and similar parts have similar numbers. This apparatus is however particularly adapted for the recovery of macromolecules from an electrophoretic gel when the portion of the gel containing the macromolecules is excised from the gel slab, macerated, and the fragments of gel 101 placed in the gel receiving receptacle 24. The membranes are angled to the horizontal to minimize any non-uniformity of the electrophoretic current due to the presence of air bubbles in the buffer solution.

The following example illustrates the operation of the process according to the present invention. In this description the following abbreviations are used SDS=sodium dodecyl sulfate EDTA=ethylenediaminetetraacetic acid T=total polyacrylamide (acrylamide plus $N,N^1$-bisacrylamide) concentration C=proportion of $N,N^1$-bisacrylamide crosslinked to total polyacrylamide concentrations PAGE=polyacrylamide gel electrophoresis

EXAMPLE

1. Materials and methods

1.1 Electroelution Device

The electroelution device of FIGS. 1 and 2 was fitted onto the end of a 3 mm thick slab gel. The paper membranes were impregnated with polyacrylamide and separated by a 0.5 mm gap to form the recovery space. The top membrane was embedded in 4% T, 2.6% C polyacrylamide and the lower one in 35% T, 14% polyacrylamide; thus proteins of approximately $M_r$ 10,000 to 1,000,000 could enter the compartment but could not pass through the lower membrane. Both ends of the recovery space were connected to fine-bore inlet and outlet tubing. Electrode buffer was perfused through this space either continuously (0.25 mL/min) or intermittently (average rate 0.025 mL/min, chamber emptied for 40 s. each 600 s.). Alternatively, quite acceptable fractionations could be obtained by manually emptying the compartment at suitable intervals using a syringe. Continuously eluted protein was collected in 2.5–5.0 mL fractions and elution profiles (and pooling of fractions for analyses) were assessed by measurement of protein absorbance at 280 nm.

Care was needed to avoid bubble formation between the gel and the top membrane, otherwise discontinuities in the electric field lead to uneven elution of protein fronts and poor resolution. Bubble formation can be readily avoided by filling the trough above the upper membrane with a few millilitres of buffer before sliding the slab gel into place.

1.2 Electrophoresis gels and buffer systems

The gels used for nondenaturing buffer electrophoresis were purchased from Gradipore Ltd. Sydney as follows: (1) 5% T, 3.3% C, uniform polyacrylamide gel, or (2) 2.5–13% T linear gradient gel. SDS gels were prepared the day before use and contained 8.5% T, 0.8% C or 13.75% T, 0.8% C or 18% T, 0.8% C. All experiments described used gels 72×75×3 mm.

Buffer systems used for nondenaturing electrophoresis were sodium lactate, pH 3.1 (containing 4 mM Na+ions) for cathodic runs and 82.5 mM Tris- 8.1 mM borate - 2.7 mM disodium ethylenediaminetetroacetic acid (EDTA), pH 8.3 at 20° for anodic electrophoresis. Sample proteins in these experiments (10–25 mg total loading in 200–500 uL) were dissolved in the appropriate buffer containing 20% glycerol. All SDS-electrophoresis experiments employed a discontinuous buffer system, adapted from Laemmli's method. The electrode buffer was 25 mM Tris-glycine, pH 8.3, containing 0.1% SDS. Proteins were "stacked" in a 3% T gel containing Tris-HCl buffer, pH 6.8. Samples were extracted in a similar pH 6.8 buffer, containing 10% glycerol, 4% SDS and 40 mM dithiothreitol. For high (2.5 mg/mL or greater) protein loadings, concentrations of the latter three reagents were double. All experiments were performed at room temperature, although the equipment may be used at 4° C.

1.3 Concentration and analysis of fractionated proteins

Protein-containing fractions were concentrated to 0.5–10 mg/mL by either (1) ultrafiltration (UM 10 membranes, Amicon, Danvers, Mass., USA); (2) concentration using 1 g/5 mL Sephadex G-25 (Pharmacia, Uppsala, Sweden) or (3) by lyophilization following dialysis. Samples were analyzed either by gradient gel electrophoresis on 2.5–27% T gels (Gradipore Pty. Ltd., Sydney) or SDS-PAGE using 15% T, 3% C, 1.5 mm thick gels.

1.4 Sources of proteins

Chymotrypsinogen A (bovine pancreas), ovalbumin (hen egg), ribonuclease A (bovine pancreas) and serum albumin (bovine) were purchased from Pharmacia, carbonic anhydrase (bovine erythrocyte), myoglobin (equine) from BDH and ovotransferrin and alpha-lactalbumin (bovine) from Sigma (St Louis, Mo., USA). Molecular weight and isoelectric point data are from information provided by the suppliers or from the reviews of Righetti and coworkers (J. Chromatog. 1981, 220, 115–194 and 1976, 127, 1–28).

2 Results

2.1 Preparative SDS electrophoresis

Initial experiments examined the relationship between the combination of applied voltage (37.5 or 75V) and polyacrylamide concentration (8.5% T or 18% T) in the resolving gel, on the resolution of a mixture of 2.5 mg each of ribonuclease A ($M_r$ 13,700), chymotrypsinogen A ($M_r$ 25,500), ovalbumin ($M_r$ 43,000) and bovine serum albumin ($M_r$ 67,000). In each of these experiments, proteins eluted in order of increasing molecular weight. Small proteins were eluted in a few hours from a 7 cm long resolving gel; larger proteins required overnight electrophoresis. Best temporal resolution of proteins was found using the higher gel concentration and lower voltage. However, while the two lower molecular weight proteins were resolved from each other and the buffer front under these conditions, excessive dilution (samples 25 ug/mL protein) of ovalbumin and serum occurred if continuous perfusions were used. These larger proteins were well resolved without excessive dilution, using 8.5% T gels, but in these cases, ribonuclease A and chymotrypsinogen A ran close to the buffer front. Clearly, the elution conditions should be optimized to suit the electrophoretic mobility of the component of interest, using experience with proteins of known mobilities. The maximum applicable voltage at a particular gel concentration depends on the gel thickness (3 mm in this case) and the heat dissipation capacity of the electrophoresis apparatus.

With the use of discontinuous buffer systems, refractive index changes upon elution of the buffer front (22) together with tracking dye, produced an artefactual absorbance peak. This peak could be distinguished from protein peaks by a test run in the absence of sample. The appearance of tracking dye was useful in determining an appropriate time to commence sample collection. Routinely, 10 mg of protein was used with the 72mm×75mm×3 mm gels, which have a cross-sectional area of about 215 mm². However, 20 mg of protein could be fractionated with little loss of resolution or alteration of retention time.

The reproducibility of elution times (=retention times on the gel) between experiments was studied using ovalbumin and serum albumin. For a given gel concentration and applied voltage, retention times were constant for each protein within a range of about 6% from the mean (3 runs, 2 voltages). Whenever ovalbumin eluted slightly earlier or later than the mean, serum albumin did so as well. The slight variations in elution times are likely due to minor variations in gel pore size or column height in these "home-made" gels and minor variations in applied voltage and ambient temperature during the experiment. These results indicate that the elution time of a protein of previously determined apparent $M_r$ in SDS-PAGE could be predicted with reasonable accuracy, allowing batchwise collection.

Proteins which have lower-than-expected mobilities for their $M_r$ in SDS-PAGE also have higher elution times in the preparative system. For example, wheat alpha-, beta- and gamma-gliadins ($M_r$ 30,000–37,000)

proteins having low mobility on SDS gels due to high proline contents, had elution times of 350–400 min (8.5% gel, 50V). These elution times resemble ovalbumin ($M_r$ 43,000, 360 min) more closely than chymotrypsinogen A ($M_r$ 25,000, 280 min).

2.2 Nondenaturing preparative PAGE

Initial experiments using 2.5–13% polyacrylamide gradient gels and Tris-borate EDTA buffer separated ovalbumin (pI 4.7, $M_r$ 43,000), bovine serum albumin (pI 4.9, $M_r$ 67,000) and ovotransferrin (pI 6.2, $M_r$ 77,000) with good resolution and in order of increasing molecular mass. However, certain proteins with less acidic isoelectric points were eluted rather slowly; for example, myoglobin (pI 7.1–7.5, $M_r$ 17,500) eluted after serum albumin. Some basic proteins have a positive charge at pH 8.3 (eg. chymotrypsinogen A, pI 9.2 and ribonuclease A, pI 9.3) and did not enter the separating gel in anodic runs at this pH. The likely elution behaviour of these proteins could be predicted from a preliminary analytical run on a gel of identical polyacrylamide gradient. Using commercially available gradient gels, elution times of standard proteins in Tris-borate - EDTA buffers were very reproducible.

| Protein | $M_r$ | Voltage applied | Run 1 | 2 | 3 |
|---|---|---|---|---|---|
| alpha-lactalbumin | 14400 | 75 | 250 | 250 | 215 |
| ovalbumin | 43000 | 75 | 260 | 275 | 260 |
|  |  | 100 | 160 | 168 |  |
| bovine serum albumin | 67000 | 75 | 400 | 395 | 385 |
|  |  | 100 | 240 | 220 | 225 |

Many groups have used PAGE at alkaline pH to analyse serum proteins. In preparative experiments, serum was electrophoresed 20 hr at 200V on a 5% T gel in Tris-borate—EDTA, pH 8.3. Fractions collected were analyzed on a gradient gel and demonstrated reasonably good separation of albumin from other components, and enrichment of other proteins in specific fractions, for example haptoglobins and alpha-2-macroglobulin. Staining of the preparative gel after the run revealed a heavy band near the origin, likely corresponding to lipoprotein and aggregated components. Using a 8.25 mM Tris-1.1 mM borate - 2.7 mM disodium EDTA buffer, pH 9.5, protein zones were eluted within 8 hr and there was less dilution of late-eluting components.

However, unacceptable swelling of the gel occurred in 25 mM Tris-barbital buffer at this pH.

To investigate whether the preparative electrophoresis unit was of use in removal of impurities from commercial protein sources, two experiments were conducted using bovine serum albumin preparations, varying in purity. Samples were run in Tris-borate-EDTA, pH 8.3 on 2.5–13% gradient gels. In both experiments run at 100V, a major peak, which upon analysis yielded a single band corresponding to albumin, eluted at about 240 min. Using the cruder preparation (serum Fraction V, Sigma A-7906) this major peak accounted for 52% of the material recovered after dialysis and lyophilization. The overall yield for a 25 mg loading was 79%. Three other peaks were observed in the Fraction V eluate - a fast eluting peak (proteolytic breakdown products of albumin?), a peak after the major albumin peak (albumin dimer?) and a late eluting peak corresponding to immunogolbulins. In the fractionation of the purer source of albumin (Signa A-7030, fatty acid and globulin free), the late-eluting peak was absent and the early peak was very small.

At pH 3.1, most common proteins bear significant positive change and can be fractionated by cathodic electrophoresis, although some proteins such as some globulins and serum proteins are denatured under these conditions. The effects of voltage on resolution of four proteins (ribonuclease A, chymotrypsinogen A, ovalbumin and bovine serum albumin) were studied in this system.

| Protein | $M_r$ | Elution times 25 V | 50 V | 100 V |
|---|---|---|---|---|
| Ribonuclease A | 13700 | 410 | 230 | 160 |
| Chymotrypsinogen A | 25500 | 490 | 280 | 190 |
| Ovalbumin | 43000 | 640 | 360 | 220 |
| Bovine Serum Albumin | 67000 | 1090 | 710 | 340 |

At 100V, bovine albumin was separated from the other components (which overlapped). Resolution of the first three peaks improved at 50V and 25V. However, at 25V, the albumin peak was diluted significantly, occupying 100 mL. Protein recoveries, calculated for this series of experiments, varied between 73% (25V run) and 93% (50V run). Recoveries below 70% occurred after 6–10 uses of the membranes, and indicated need for their replacement. Extensive dilution could be avoided either by increasing voltage in a stepwise or continuous fashion or by the use of intermittent elution (FIG. 5). Using the latter approach, pure components could be obtained by analysis of "cuts" of peaks.

I claim:

1. In an electroelution device used in the preparative scale recovery of macromolecules from an electrophoretic gel and installed between the electrodes of an electrophoretic cell, the improvement comprising said device comprising a gel receiving receptacle, an aperture in the base of the receptacle, a first membrane substantially permeable to the macromolecules desired to be recovered covering the aperture, a second membrane, substantially impermeable to the macromolecules to be recovered but permeable to electrolyte molecules in a buffer solution used in electrophoresis, lying in spaced apart array with the first membrane to define therebetween a recovery space, and means to allow the periodic or continuous withdrawal of buffer solution and macromolecules from the recovery space.

2. An electroelution device as claimed in claim 1 in which the gel receiving receptacle is adapted to receive an end of an electrophoretic gel slab.

3. An electroelution device as claimed in claim 1 in which the gel receiving receptacle is adapted to receive a macerated portion of an electrophoretic gel containing an electrophoretically separated macromolecule.

4. An electroelution device as claimed in claim 1 in which the gel receiving space in a cross section transversely to the path of an electrophoretic current passing through the device and the dimensions of one pair of sides of that rectangle is substantially larger than the dimensions of the other pair of sides.

5. An electroelution device as claimed in claim 1 in which one or both of the membranes is formed of paper impregnated with polyacrylamide.

6. An electroelution device as claimed in claim 1 in which the first membrane has a pore size such that molecules of molecular weights of from 10,000 to 1,000,000 may pass therethrough.

7. An electroelution device as claimed in claim 1 in which the withdrawal of macromolecules from the recovery space includes a pair of tubes one of which communicates with each end of the recovery space.

8. A method for the preparative scale recovery of macromolecules from an electrophoretic gel comprising placing an electrophoretic gel containing macromolecules to be recovered into the gel receiving receptacle of an electroelution device according to claim 1, applying an electric potential across the device to cause the macromolecules to migrate through the first membrane into the recovery space, and recovering the macromolecules from the recovery space of the said device.

9. A method as claimed in claim 8 in which the macromolecules are proteins.

10. A method as claimed in claim 8 in which the macromolecules are periodically withdrawn from the recovery space and the space then flushed with buffer prior to the collection of further macromolecules in the recovery space.

* * * * *